(12) United States Patent
Ding et al.

(10) Patent No.: US 12,636,420 B2
(45) Date of Patent: May 26, 2026

(54) REGIONAL CITRATE ANTICOAGULATION INFUSION SYSTEM, CONTROL METHOD AND SYSTEM, AND MEDIUM

(71) Applicant: SHANGHAI SUPERB MEDICAL TECHNOLOGY CO., LTD, Shanghai (CN)

(72) Inventors: Feng Ding, Shanghai (CN); Chaobin Wang, Shanghai (CN); Damin Ding, Shanghai (CN)

(73) Assignee: SHANGHAI SUPERB MEDICAL TECHNOLOGY CO., LTD, Shanghai (CN)

( * ) Notice: Subject to any disclaimer, the term of this patent is extended or adjusted under 35 U.S.C. 154(b) by 27 days.

(21) Appl. No.: 18/276,260

(22) PCT Filed: Jul. 8, 2021

(86) PCT No.: PCT/CN2021/105111
§ 371 (c)(1),
(2) Date: Aug. 8, 2023

(87) PCT Pub. No.: WO2022/193488
PCT Pub. Date: Sep. 22, 2022

(65) Prior Publication Data
US 2024/0115788 A1 Apr. 11, 2024

(30) Foreign Application Priority Data

Mar. 17, 2021 (CN) .......................... 202110285257.6

(51) Int. Cl.
*A61M 1/36* (2006.01)
*A61M 1/34* (2006.01)

(52) U.S. Cl.
CPC ........ *A61M 1/3672* (2013.01); *A61M 1/3406* (2014.02); *A61M 1/3413* (2013.01);
(Continued)

(58) Field of Classification Search
None
See application file for complete search history.

(56) References Cited

U.S. PATENT DOCUMENTS

2007/0066928 A1* 3/2007 Lannoy ............... A61M 1/3612
604/6.07
2018/0050148 A1 2/2018 Kenley

FOREIGN PATENT DOCUMENTS

CN 102309785 A 1/2012
CN 203139210 U 8/2013
(Continued)

OTHER PUBLICATIONS

"Machine Translation of WO2018040324", Ding et al., WO2018040324 A1, published 2018, 61 total pages. (Year: 2018).*

*Primary Examiner* — Jonathan M Peo
(74) *Attorney, Agent, or Firm* — IPRTOP LLC

(57) ABSTRACT

A method for controlling an infusion rotation speed of a citrate pump comprises: collecting parameters of the regional citrate anticoagulation infusion system (S101), the parameters include blood flow velocity and red blood cell hematocrit; determining a citrate infusion volume per unit time based on the parameters (S102); and controlling the infusion rotation speed of the citrate pump based on the citrate infusion volume per unit time (S103). A method for controlling an infusion rotation speed of a calcium pump includes: determining an amount of calcium supplementation required for the regional citrate anticoagulation infusion system (S201); and controlling the infusion rotation speed of the calcium pump according to the amount of calcium supplementation (S202). The citrate infusion volume per unit time and the amount of calcium supplementation required by the regional citrate anticoagulation infusion system is determined through specific formulas.

10 Claims, 7 Drawing Sheets

(52) U.S. Cl.
CPC . *A61M 2205/18* (2013.01); *A61M 2205/3365* (2013.01); *A61M 2205/3379* (2013.01); *A61M 2230/207* (2013.01)

(56) References Cited

FOREIGN PATENT DOCUMENTS

| | | | |
|---|---|---|---|
| CN | 106267408 | A | 1/2017 |
| CN | 107617132 | A | 1/2018 |
| CN | 113018546 | A | 6/2021 |
| WO | WO 2018040324 | A1 | 3/2018 |

* cited by examiner

S2011

Calculating the diffusible calcium clearance Cln-ca after selecting the membrane area for the dialyzer

S2012

Calculating the amount of calcium cleared in extracorporeal circulation per hour through the above diffusible calcium clearance Cln-ca

REGIONAL CITRATE ANTICOAGULATION INFUSION SYSTEM, CONTROL METHOD AND SYSTEM, AND MEDIUM

FIELD OF THE INVENTION

The present disclosure relates to the technical field of medical devices and intelligent control, in particular, to a regional citrate anticoagulation infusion system, a control method and system, and a medium.

BACKGROUND OF THE INVENTION

Regional citrate anticoagulation (RCA) has shown effectiveness in in vitro anticoagulation. Specifically, the patient's blood is drawn from the body, afterward, it passes through a dialyzer and then is returned to the body. An injection of sodium citrate anticoagulant to the blood channel via a citrate infusion pump is required before the blood enters the dialyzer, and an injection of calcium chloride solution to the blood channel via a calcium chloride infusion pump is required before the blood returns to the body to supplement the patient's lost calcium. This anticoagulation method avoids prolonged exposure to heparin and reduces the risk of bleeding. RCA is currently performed by a trial-and-error method in clinical, i.e., adjusting the infusion rate of citrate and calcium by frequent monitoring ionized calcium in vivo and extracorporeal circulation, which limits the application of RCA technology.

In order to solve the above problem, some new techniques have emerged. For example, Chinese patent CN201710640069.4 discloses a citrate anticoagulation control system applicable to continuous venovenous hemodialysis (CVVHD) process, and an apparatus and application thereof, where the citrate anticoagulation control system applicable to CVVHD process comprises a first peristaltic pump speed calculation module for calculating the infusion speed of citrate and a second peristaltic pump speed calculation module for calculating supplementation rate of calcium. The second peristaltic pump speed calculation module comprises a first-stage speed calculation unit for calculating the sum of the amount of calcium removed in extracorporeal dialysis and the amount of calcium accumulated in the body, and a second-stage speed calculation unit for calculating the amount of calcium removed in extracorporeal dialysis. The citrate anticoagulation apparatus comprises the above-mentioned citrate anticoagulation control system applicable to CVVHD process.

The citrate anticoagulation control system and citrate anticoagulation apparatus in CN201710640069.4 enable automated control of the citrate pump and calcium pump, thus saving manpower and bringing about accuracy, safety, and stability. However, they are only applicable to citrate anticoagulation therapy in CVVHD mode.

SUMMARY OF THE INVENTION

The present disclosure provides a regional citrate anticoagulation infusion system, a control method and system, and a medium, which achieves automated control of the citrate pump and/or calcium pump and can be applicable to citrate anticoagulation therapy in continuous venovenous hemodiafiltration (CVVHD) mode and intermittent hemodialysis (iHD) mode.

A first aspect of the present disclosure provides a method for controlling an infusion rotation speed of a citrate pump, comprising: collecting a plurality of parameters of a regional citrate anticoagulation infusion system, the plurality of parameters comprises blood flow velocity and red blood cell hematocrit; determining a citrate infusion volume per unit time based on the plurality of parameters; and controlling an infusion rotation speed of the citrate pump based on the citrate infusion volume per unit time.

The citrate infusion volume per unit time is obtained through the following equation:

$$Qcit \text{ (mmol/h)}=4\text{-}5 \text{ (mmol/L)} \times Qb \text{ (ml/min)} \times (1-Hct\%)$$

In the equation, Qcit is the citrate infusion volume per unit time, Qb is the blood flow velocity, and Hct is the red blood cell hematocrit.

A second aspect of the present disclosure provides a method for controlling an infusion rotation speed of a calcium pump, comprising: determining an amount of calcium supplementation required for a regional citrate anticoagulation infusion system; and controlling an infusion rotation speed of the calcium pump according to the amount of calcium supplementation.

The determining of the amount of calcium supplementation required for a regional citrate anticoagulation infusion system includes:

for a post-dilution CVVHD model, calculating an amount of calcium supplementation required in each stage of a two-stage calcium supplement model;

an amount of calcium supplementation required in the first stage is obtained through the following equation:

$$Qca1(\text{mmol}/h) = \frac{fa \times \text{Cca\_T} \times Cln - ca \times 60)}{1000} + fb \times Csys(t) \times BW(kg) \times 25\%$$

an amount of calcium supplementation required in the second stage is obtained through the following equation:

$$Qca2(\text{mmol}/h) = \frac{fa \times \text{Cca\_T} \times Cln - ca \times 60}{1000}$$

where Qca1 is the amount of calcium supplementation required in the first stage, Qca2 is the amount of calcium supplementation required in the second stage, fa is a fraction of dispersable calcium at the upstream of the dialyzer after citrate infusion at the arterial end, Cca_T is a total calcium concentration at the upstream of the dialyzer after citrate infusion, Cln-ca is a dispersable calcium clearance, fb is a correlation coefficient between the accumulated calcium concentration and the citrate concentration, Csys(t) is a concentration of citrate at different time, and BW is a weight of a patient;

for an intermittent hemodialysis (iHD) mode, the amount of calcium supplementation is an amount of calcium cleared in extracorporeal circulation;

the dispersable calcium clearance Cln-ca is calculated after selecting the membrane area for the dialyzer;

when the membrane area is less than 1.2 $m^2$, Cln-Ca=0.7944×(Qb×0.43+80.5)×(1−Hct)+2.2421+0.46× Quf;

when the membrane area ranges from 1.2 to 1.8 $m^2$, Cln-Ca=0.7944×(Qb×0.29+95)×(1−Hct)+2.2421+ 0.46×Quf;

when the membrane area is greater than 1.8 m², Cln-Ca=0.7944×(Qb×0.53+75.5)×(1−Hct)+2.2421+0.46×Quf;

the amount of calcium cleared in extracorporeal circulation per hour can be calculated based on the above dispersable calcium clearance Cln-ca through the following equation:

$$Eca\ (\text{mmol/L}) = fa \times Cca\_T \times Cln\text{-}ca \times 60/1000$$

where Qb is the blood flow velocity; Quf is the ultrafiltration rate; and Eca (mmol/L) is the amount of calcium cleared in extracorporeal circulation per hour.

A third aspect of the present disclosure provides a module for controlling an infusion rotation speed of a citrate pump, including:

a parameter acquisition module, for collecting a plurality of parameters of a regional citrate anticoagulation infusion system, where the plurality of parameters comprises blood flow velocity and red blood cell hematocrit;

an infusion volume determination module, for determining a citrate infusion volume per unit time based on the plurality of parameters;

a citrate pump speed control module, for controlling an infusion rotation speed of the citrate pump based on the citrate infusion volume per unit time;

where the infusion volume determination module obtains the citrate infusion volume per unit time based on the following equation:

$$Qcit\ (\text{mmol/h}) = 4\text{–}5\ (\text{mmol/L}) \times Qb\ (\text{ml/min}) \times (1\text{–}Hct\%)$$

where Qcit is the citrate infusion volume per unit time, Qb is the blood flow velocity, and Hct is the red blood cell hematocrit.

A fourth aspect of the present disclosure provides a module for controlling an infusion rotation speed of a calcium pump, including:

a calcium supplementation determination module, for determining an amount of calcium supplementation required for a regional citrate anticoagulation infusion system;

a calcium pump speed control module, for controlling an infusion rotation speed of the calcium pump according to the amount of calcium supplementation;

where the calcium supplementation determination module determines the amount of calcium supplementation required for the regional citrate anticoagulation infusion system according to the following equations;

for a post-dilution CVVHD model, an amount of calcium supplementation required in each stage of a two-stage calcium supplement model is calculated;

an amount of calcium supplementation required in the first stage is obtained through the following equation:

$$Qca1\,(\text{mmol/h}) = \frac{fa \times Cca\_T \times Cln - ca \times 60)}{1000} + fb \times Csys(t) \times BW(kg) \times 25\%$$

an amount of calcium supplementation required in the second stage is obtained through the following equation:

$$Qca2\,(\text{mmol/h}) = \frac{fa \times Cca\_T \times Cln - ca \times 60}{1000}$$

where Qca1 is the amount of calcium supplementation required in the first stage, Qca2 is the amount of calcium supplementation required in the second stage, fa is a fraction of dispersable calcium at the upstream of the dialyzer after citrate infusion at the arterial end, Cca_T is a total calcium concentration at the upstream of the dialyzer after citrate infusion, Cln-ca is a dispersable calcium clearance, fb is a correlation coefficient between the accumulated calcium concentration and the citrate concentration, Csys(t) is a concentration of citrate at different time, and BW is a weight of a patient;

for an intermittent hemodialysis (iHD) mode, the amount of calcium supplementation is an amount of calcium cleared in extracorporeal circulation;

the dispersable calcium clearance Cln-ca is calculated after selecting the membrane area for the dialyzer;

when the membrane area is less than 1.2 m², Cln-Ca=0.7944×(Qb×0.43+80.5)×(1−Hct)+2.2421+0.46×Quf;

when the membrane area ranges from 1.2 to 1.8 m², Cln-Ca=0.7944×(Qb×0.29+95)×(1−Hct)+2.2421+0.46×Quf;

when the membrane area is greater than 1.8 m², Cln-Ca=0.7944×(Qb×0.53+75.5)×(1−Hct)+2.2421+0.46×Quf;

the amount of calcium cleared in extracorporeal circulation per hour can be calculated based on the above dispersable calcium clearance Cln-ca through the following equation:

$$Eca\ (\text{mmol/L}) = fa \times Cca\_T \times Cln\text{-}ca \times 60/1000$$

where Qb is the blood flow velocity, Quf is the ultrafiltration rate, and Eca (mmol/L) is the amount of calcium cleared in extracorporeal circulation per hour.

A fifth aspect of the present disclosure provides a method for controlling a regional citrate anticoagulation infusion, including:

controlling of an infusion rotation speed of a citrate pump, and controlling of an infusion rotation speed of a calcium pump;

where the controlling of the infusion rotation speed of the citrate pump and the controlling of the infusion rotation speed of the calcium pump are realized by the method for controlling the infusion rotation speed of the citrate pump and the method for controlling the infusion rotation speed of the calcium pump, respectively.

A sixth aspect of the present disclosure provides a control module for a regional citrate anticoagulation infusion, comprising:

a control module for an infusion rotation speed of a citrate pump, and a control module for an infusion rotation speed of a calcium pump;

where the control module for the infusion rotation speed of the citrate pump and the control module for the infusion rotation speed of the calcium pump are the module for controlling the infusion rotation speed of the citrate pump and the module for controlling the infusion rotation speed of the calcium pump, respectively.

A seventh aspect of the present disclosure provides a regional citrate anticoagulation infusion system, comprising:

a citrate pump, for infusing a sodium citrate anticoagulant;

a calcium pump, for infusing a calcium chloride solution;

and a controller, for controlling infusion speeds of the citrate pump and the calcium pump.

In an embodiment, the controller includes:

a sampling and executing module, for collecting external signals and executing controller commands, which collects a plurality of parameters from an infusion tube, receives commands from the controller regarding the infusion speed of the citrate pump and the calcium pump, and controls a drive motor to make the citrate pump and calcium pump work at a specified speed, respectively;

a therapeutic analysis module, for regularly measuring a flow volume of the citrate pump and the calcium pump and feeding each flow volume back to the control modules for the infusion rotation speeds of the citrate pump and the calcium pump, where the control modules control rotation speeds of the citrate pump and the calcium pump according to the flow volumes and predetermined parameters.

In an embodiment, the controller further comprises a safety module, for analyzing the running condition of a real-time monitoring device through sampling data and prompting alarm and operation according to an accident occurred in a treatment process proposed by an accident occurrence-treatment module.

The sampling and executing module, the therapeutic analysis module, and the safety module run in parallel and independently exchange data with the database.

In an embodiment, the therapeutic analysis module can receive and analyze in real-time the data signals transmitted from the sampling and executing module.

In an embodiment, the therapeutic analysis module can record data to a database or share data for recording and reading treatment records and treatment incidents by external devices.

In an embodiment, the therapeutic analysis module can analyze patient information and therapeutic information according to a predetermined procedure, calculate in real time the desired citrate and calcium chloride infusion speed according to a two-stage theoretical model, and transmit signals of the calculated infusion speeds to the sampling and executing module;

In an embodiment, the therapeutic analysis module can exchange the sampling data in real-time with the safety module, analyze whether the device is in normal operation according to the accident treatment opinion and prompt protective actions and audible and visual alarms in response to the operation status of the device.

In an embodiment, a fuzzy adaptive tuning PID control is used for a single citrate pump and a single calcium pump, respectively. According to the response of the control system, a fuzzy inference is applied with reference to the fuzzy control rules stored in advance in the computer to automatically achieve the optimal adjustment of the PID parameters of the single citrate pump and the single calcium pump, respectively.

An eighth aspect of the present disclosure provides an electronic device, including a memory, a processor, and a computer program stored in the memory and executed on the processor, when the processor executes the computer program, one of the following methods is performed:

6 the method for controlling the infusion rotation speed of the citrate pump;

the method for controlling the infusion rotation speed of the calcium pump; and the method for controlling the regional citrate anticoagulation infusion.

A ninth aspect of the present disclosure provides a computer-readable storage medium, having a computer program stored thereon, when the computer program is executed by a processor, one of the following methods is performed:

the method for controlling the infusion rotation speed of the citrate pump;

the method for controlling the infusion rotation speed of the calcium pump; and the method for controlling the regional citrate anticoagulation infusion.

The present disclosure has at least one of the following beneficial effects:

The regional citrate anticoagulation infusion system, the control method and system, and the medium in the present disclosure achieve automated control of the citrate pump and/or calcium pump and keep the rotation speed stable and controllable. Furthermore, patient safety is ensured by timely alarm and emergency control when abnormal conditions occur.

The above regional citrate anticoagulation infusion system, the control method and system, and the medium in the present disclosure can be applied to determine the rotation speeds of the citrate pump and calcium pump in CVVHDF and iHD modes to achieve precise control of the infusion speeds.

BRIEF DESCRIPTION OF DRAWINGS

A detailed description of non-limiting embodiments is provided with reference to the following drawings. For those skilled in the art, other features, objects, and advantages may be obtained without effort.

US 12,636,420 B2

7

Figure 13:
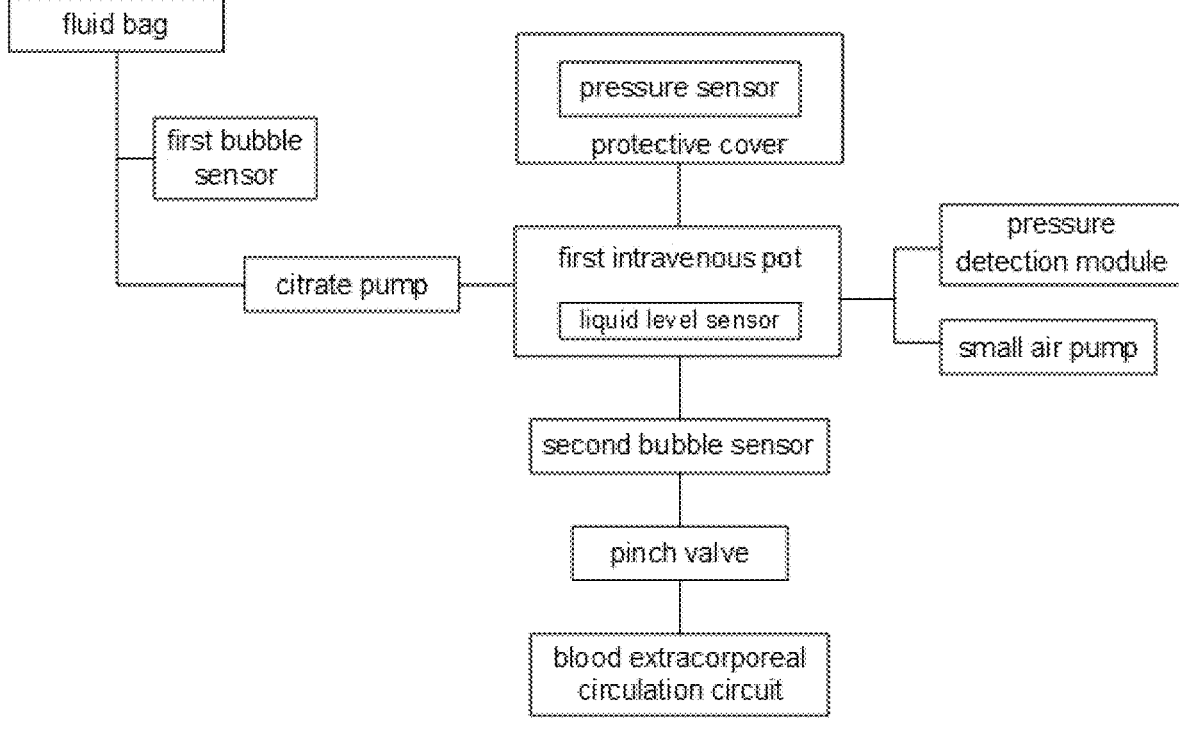

FIG. 13 is a schematic diagram of a citrate infusion system in a regional citrate anticoagulation infusion system in one embodiment.

DETAILED DESCRIPTION OF THE INVENTION

The present disclosure will be described in detail by using the embodiments below. The following embodiments are intended to assist those skilled in the art to further understand the present disclosure, and not to limit the present disclosure. It should be noted that to a person of ordinary skill in the art, a number of variations and changes can be made without departing from the conception of the present disclosure, which still falls within the protection scope of the present disclosure.

In regional citrate anticoagulation, the amount of citrate and calcium supplementation under various modes and dosages of RCA is precisely and quantitatively controlled based on the two-stage calcium supplement model of regional citrate anticoagulation combined with the citrate pharmacokinetics theory and the blood purification clearance kinetics theory, and the main principles are as follows:

1. The infusion speed of citrate during RCA is correlated with the flow rate of plasma in extracorporeal circulation.
2. The rate of calcium supplementation during blood purification technique (e.g., continuous renal replacement therapy (CRRT)) RCA with low solute clearance has two stages, which is characterized by the heterogeneity of calcium requirements, i.e., more calcium is required in the first stage and less calcium in the second stage. The reason for this is that the citrate clearance during inefficient blood purification is low, which leads to the accumulation of citrate in the patient's body, citrate is mostly in the form of calcium citrate in the body, and the steady state of citrate and blood calcium is reached after 3 to 5 half-lives of citrate metabolism in the body. Therefore, during the first stage of RCA-CRRT, calcium supplementation includes cleared calcium in extracorporeal circulation and accumulated calcium, whereas during the subsequent second stage, only cleared calcium in extracorporeal circulation is included.
3. The concentration of the effluent liquid calcium does not equilibrate with that of the blood calcium during CRRT, i.e., the calcium clearance in extracorporeal circulation is correlated with the dose and mode of CRRT.
4. The amount of calcium supplementation of high-efficiency blood purification techniques (e.g., IHD) is mainly correlated with the clearance in extracorporeal circulation, and there is a correlation between the calcium clearance, and the creatinine clearance and phosphate clearance of the dialyzer.

Figure 1:
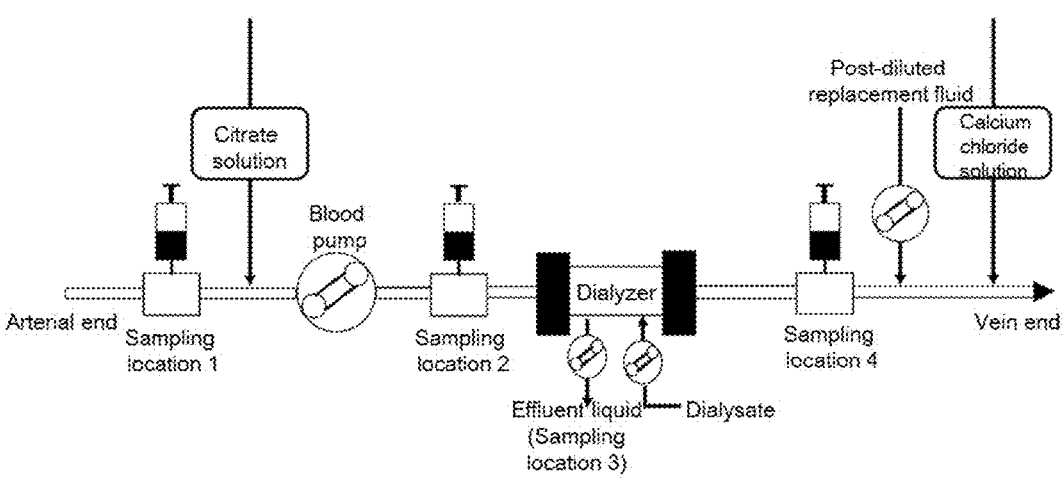
FIG. 1 is a schematic diagram of a citrate anticoagulation in a post-dilution CVVHDF mode.

FIG. 1 is a schematic diagram of a citrate anticoagulation in post-dilution CVVHDF mode. According to the principle of citrate anticoagulation in post-dilution CVVHDF mode, the key parameter that determines the citrate infusion speed is the calcium load in extracorporeal circulation. When the concentration of ionized calcium in the body is within the normal range, 4.0-5.0 mM citrate per liter of plasma is required to reduce the ion concentration to 0.2-0.4 mmol/L in extracorporeal circulation.

Figure 2:
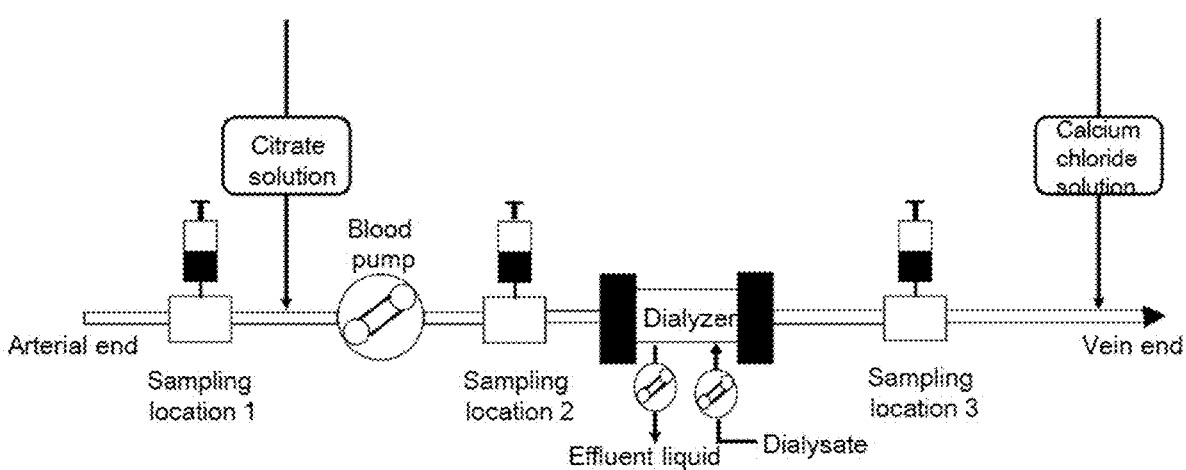
FIG. 2 is a schematic diagram of an intermittent hemodialysis (iHD) mode.

FIG. 2 is a schematic diagram of an intermittent hemodialysis (iHD) mode. The key parameter that determines the citrate infusion speed is the calcium load in extracorporeal circulation. When the concentration of ionized calcium in the body is within the normal range, 4.0-5.0 mM citrate per liter of plasma is required to reduce the ion concentration to 0.2-0.4 mmol/L in extracorporeal circulation.

Based on the above principles, embodiments of the present disclosure provide a regional citrate anticoagulation infusion system, a control method and system, and a medium, for realizing automatic control of the infusion rotation speed of the citrate anticoagulant in the treatment tubes in regional citrate anticoagulation, and further for realizing automatic control of the infusion rotation speed of the calcium pump in the treatment tubes to prevent the loss of ionized calcium in the patient's body. Infusion of citrate anticoagulant and calcium supplementation at a desired rate to the patient is achieved, thereby avoiding prolonged exposure of the patient to heparin and reducing the risk of bleeding.

Figure 3:
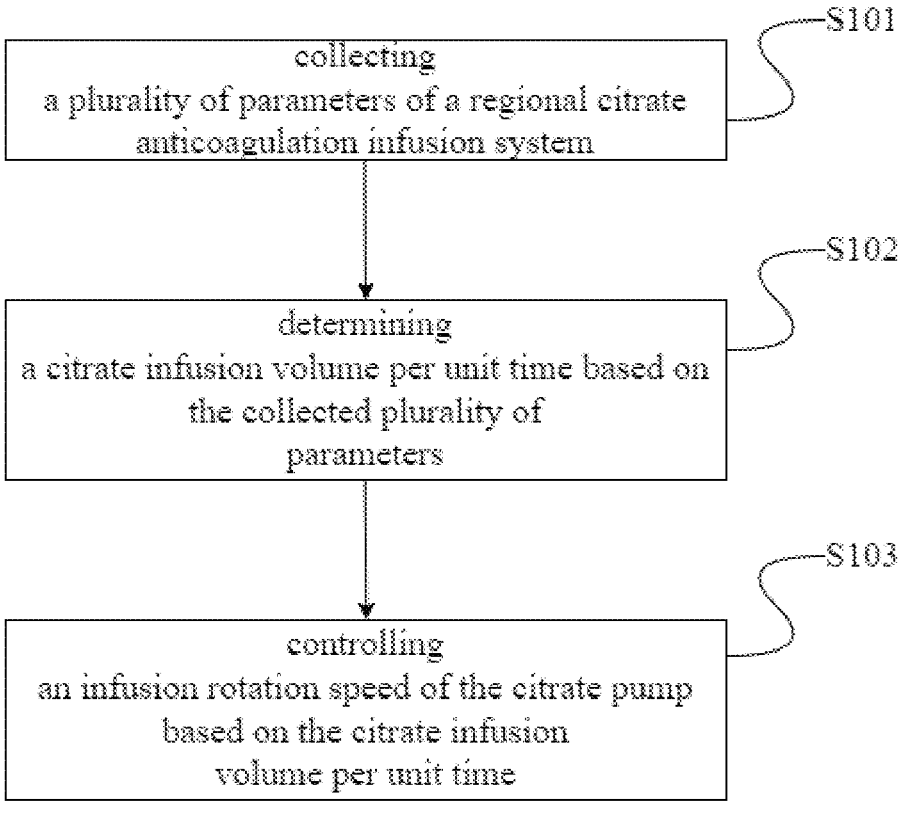
FIG. 3 is a flow chart of a method for controlling an infusion rotation speed of a citrate pump in one embodiment.

FIG. 3 is a flow chart of a method for controlling an infusion rotation speed of a citrate pump in one embodiment. In this embodiment, the method includes the following:

S101, collecting a plurality of parameters of a regional citrate anticoagulation infusion system, the plurality of parameters includes blood flow velocity and red blood cell hematocrit;

S102, determining a citrate infusion volume per unit time based on the collected plurality of parameters;

S103, controlling an infusion rotation speed of the citrate pump based on the citrate infusion volume per unit time.

In S102, the citrate infusion volume per unit time is obtained through the following equation:

$$Qcit \text{ (mmol/h)}=4\text{-}5 \text{ (mmol/L)}\times Qb \text{ (ml/min)}\times(1-Hct\%) \quad (1)$$

In the above equation, Qcit is the citrate infusion volume per unit time, Qb is the blood flow velocity, and Hct is the red blood cell hematocrit.

In S103, the amount of infused citrate per unit time is determined, and the infusion rotation speed of the citrate pump can be determined according to the model of the citrate pump, so that the infusion of citrate anticoagulant in the treatment tubes can be controlled automatically.

Figure 4:
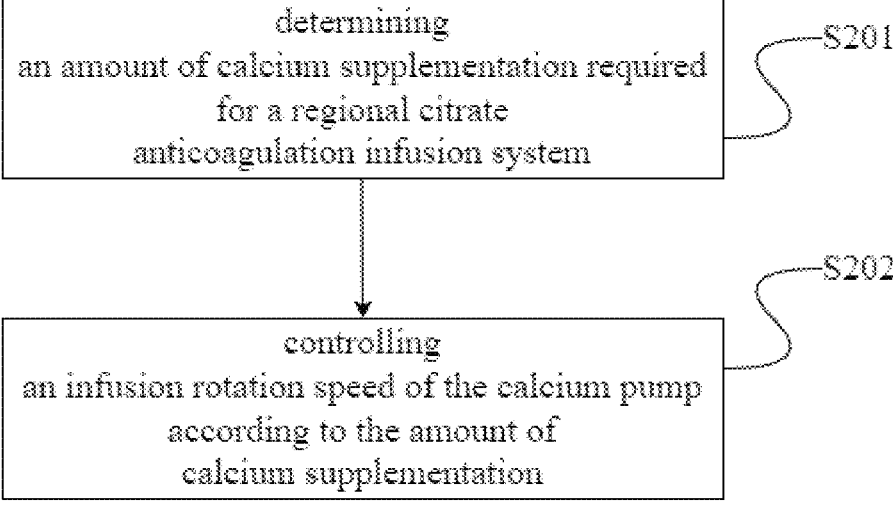
FIG. 4 is a flow chart of a method for controlling an infusion rotation speed of a calcium pump in one embodiment.

FIG. 4 is a flow chart of a method for controlling an infusion rotation speed of a calcium pump in one embodiment. In this embodiment, the method includes the following:

S201, determining an amount of calcium supplementation required for a regional citrate anticoagulation infusion system;

S202, controlling an infusion rotation speed of the calcium pump according to the amount of calcium supplementation.

In S201, for the post-dilution CVVHDF mode, a two-stage calcium supplementation equation can be simplified and quantified based on a two-stage calcium supplementation model combined with in vivo calcium accumulation, where calcium clearance in extracorporeal circulation per hour is obtained by using diffusible calcium clearance and the proportion of diffusible calcium to total calcium at the upstream of the dialyzer after citrate infusion at the arterial end. Specifically, in order to determine the amount of the calcium supplementation required for the regional citrate anticoagulation infusion system, the amount of calcium supplementation required in each stage of a two-stage calcium supplement model is calculated as follows:

An amount of calcium supplementation required in the first stage is obtained through the following equation:

$$Qca1(\text{mmol}/h) = \quad (2)$$

$$\frac{fa \times \text{Cca\_T} \times Cln - ca \times 60)}{1000} + fb \times Csys(t) \times BW(kg) \times 25\%$$

An amount of calcium supplementation required in the second stage is obtained through the following equation:

$$Qca2(\text{mmol}/h) = \frac{fa \times \text{Cca\_T} \times Cln - ca \times 60}{1000} \quad (3)$$

In the above equations, Qca1 is the amount of calcium supplementation required in the first stage, Qca2 is the amount of calcium supplementation required in the second stage, fa is a proportion of diffusible calcium at the upstream of the dialyzer after citrate infusion at the arterial end, Cca_T is a total calcium concentration at the upstream of the dialyzer after citrate infusion, Cln-ca is a diffusible calcium clearance, fb is a correlation coefficient between the accumulated calcium concentration and the citrate concentration, Csys(t) is a concentration of citrate at different time, and BW is a weight of a patient.

Figure 12:
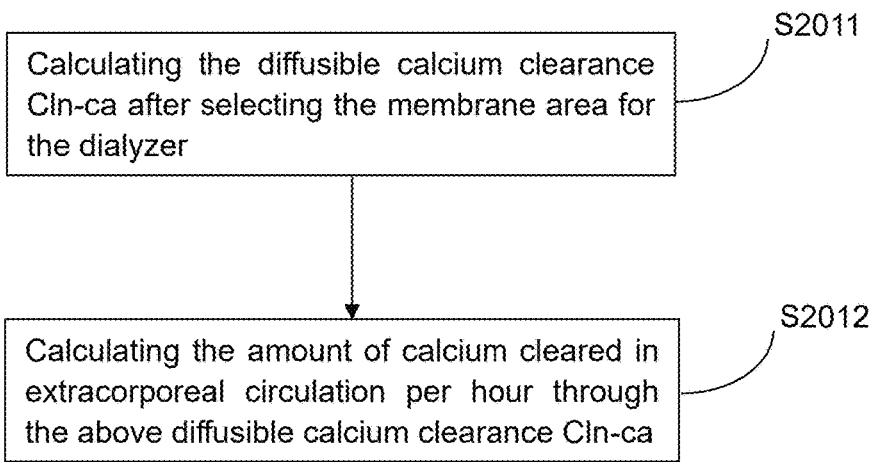
FIG. 12 is a flow chart of a method for determining an amount of calcium supplementation in a regional citrate anticoagulation infusion system in one embodiment.

In an embodiment of the present disclosure, for the intermittent hemodialysis (iHD) mode, the amount of calcium supplementation is an amount of calcium cleared in extracorporeal circulation, therefore, as shown in FIG. 12, the amount of calcium supplementation in regional citrate anticoagulation infusion system can be determined according to the following:

S2011, calculating the diffusible calcium clearance Cln-ca after selecting the membrane area for the dialyzer;

S2012, calculating the amount of calcium cleared in extracorporeal circulation per hour through the above diffusible calcium clearance Cln-ca.

Due to that there are a variety of dialyzers with an effective membrane area of 1.0-2.0 m² in IHD mode and different models of dialyzers have differences in solute clearance, the following equations are obtained by analyzing the types of dialyzers, the linear relationship between actual diffusible calcium clearance and the clearance of creatinine and phosphate for each dialyzer:

$$Cln\text{-}Ca = 0.79 \times (1 - Hct) \times (CliCr + CliP)/2 + 2.24$$
$$(R2 = 0.31, p = 0.0165) \quad (6)$$

where Cln-Ca is actual diffusible calcium clearance, CliCr is creatinine clearance, CliP is phosphate clearance, and Hct is red blood cell hematocrit.

Equation (6) works when the ultrafiltration rate is 0. In clinical treatment, the ultrafiltration rate is usually not 0, so the clearance corresponding to the ultrafiltration rate needs to be taken into consideration. According to previous studies, when the ultrafiltration rate is less than 70 ml/min, the clearance and ultrafiltration rate satisfy the following equation:

$$CIB = CIB0 + 0.46 \times Quf \quad (7)$$

In the above equation, CIB is a clearance corresponding to the actual ultrafiltration rate; CIB0 is a clearance when the ultrafiltration rate is 0, Quf is the ultrafiltration rate.

The actual ultrafiltration rate is incorporated into the above equation to yield the following:

$$Cln\text{-}Ca = 0.79 \times (1 - Hct) \times (CliCr + CliP)/2 + 2.24 + 0.46 \times Quf \quad (8)$$

When the blood flow velocity of the dialyzer is 150-300 m l/m in, the solute clearance is approximately linear with the blood flow velocity, therefore, the relationship between the solute clearance and blood flow velocity can be calculated according to the dialyzer manual, and the formula for estimating the actual diffusible calcium clearance and blood flow velocity can be obtained by incorporating the clearance formula. The effective membrane area of the dialyzers can be classified into three categories:

When the membrane area is less than 1.2 m², $$Cln\text{-}Ca = 0.7944 \times (Qb \times 0.43 + 80.5) \times (1 - Hct) + 2.2421 + 0.46 \times Quf. \quad (9)$$

When the membrane area ranges from 1.2 to 1.8 m², $$Cln\text{-}Ca = 0.7944 \times (Qb \times 0.29 + 95) \times (1 - Hct) + 2.2421 + 0.46 \times Quf. \quad (10)$$

And when the membrane area is greater than 1.8 m², $$Cln\text{-}Ca = 0.7944 \times (Qb \times 0.53 + 75.5) \times (1 - Hct) + 2.2421 + 0.46 \times Quf. \quad (11)$$

More than 80% of calcium citrate is removed by the dialyzer and little citrate accumulates because of the fast flow rate of dialysate in IHD model. Therefore, the amount of calcium supplementation in IHD is mainly the calcium removed in extracorporeal circulation. As described above, the equation for calcium clearance in extracorporeal circulation can be expressed as follows:

$$Eca \ (\text{mmol/L}) = fa \times Cca\_T \times Cln\text{-}Ca \times 60/1000 \quad (12)$$

In the above equation, Qb is the blood flow velocity, Quf is the ultrafiltration rate, and Eca (mmol/L) is the amount of calcium cleared in extracorporeal circulation per hour.

In IHD mode, the mean value of fa is 0.85, the steady-state calcium concentration (Cca_T) in the body is close to the total calcium concentration in the body at the start of treatment, and the equations for clearance (CI) are equations (9)-(11). After selecting the membrane areas of different dialyzers, the clearance (CI) is calculated, afterwards, the calcium clearance in extracorporeal circulation per hour can be calculated after incorporating into equation (12), and then the infusion rotation speed of the corresponding calcium pump can be determined.

Figure 5:
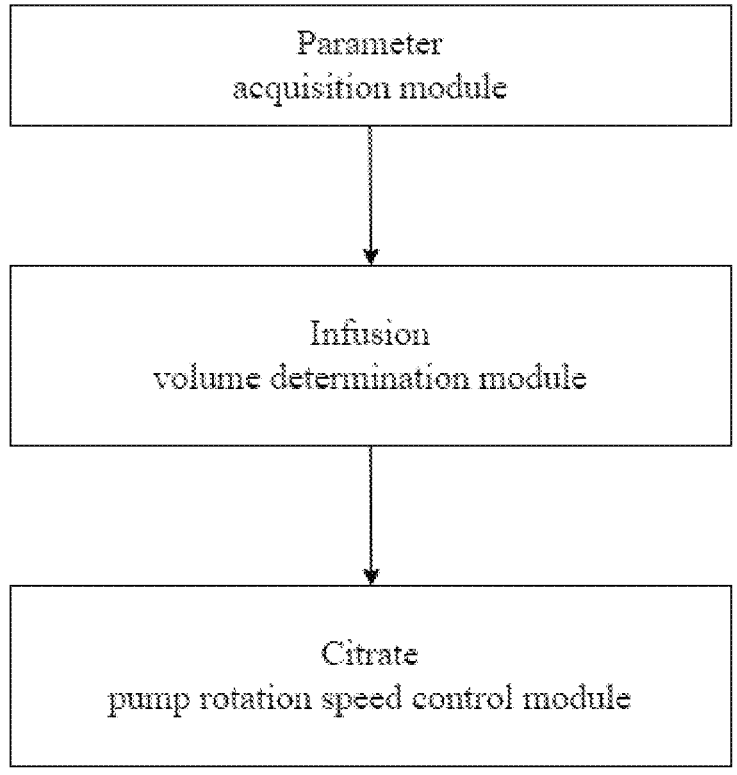
FIG. 5 is a block diagram of a module for controlling an infusion rotation speed of a citrate pump in one embodiment.

Based on the method for controlling the infusion rotation speed of the citrate pump in the above embodiment, which is also shown in FIG. 3, a control module for the infusion rotation speed of the citrate pump is correspondingly provided in another embodiment, with which the above method for controlling the infusion rotation speed of the citrate pump can be implemented. Specifically, referring to FIG. 5, the control module for the infusion rotation speed of the citrate pump comprises: a parameter acquisition module, an infusion volume determination module, and a citrate pump rotation speed control module, where the parameter acquisition module is used to collect a plurality of parameters of the regional citrate anticoagulation infusion system, the plurality of parameters includes blood flow velocity and red blood cell hematocrit, the infusion volume determination module is used to determine citrate infusion volume per unit time based on the plurality of parameters; the citrate pump speed control module is used to control the infusion rotation speed of the citrate pump based on the citrate infusion volume per unit time, and the infusion volume determination module obtains the citrate infusion volume per unit time based on equation (1).

Figure 6:
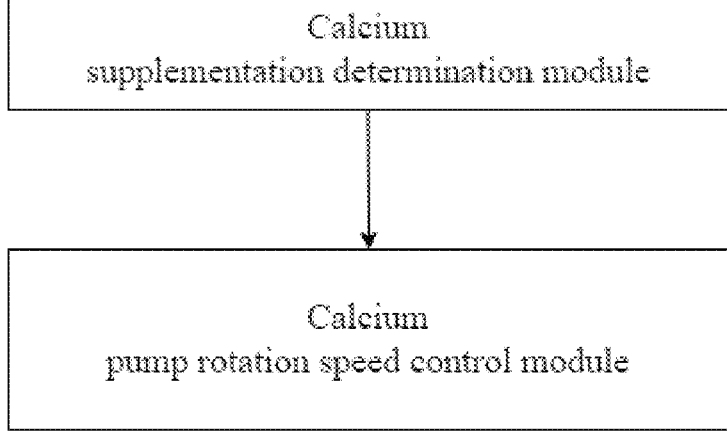
FIG. 6 is a block diagram of a module for controlling an infusion rotation speed of a calcium pump in one embodiment.

Based on the method for controlling the infusion rotation speed of the calcium pump in the above embodiment, which is also shown in FIG. 4, a control module for the infusion rotation speed of the calcium pump is correspondingly provided in another embodiment, with which the above method for controlling the infusion rotation speed of the calcium pump can be implemented. Specifically, referring to FIG. 6, the control module for the infusion rotation speed of the calcium pump comprises: a calcium supplementation determination module and a calcium pump rotation speed control module, where the calcium supplementation determination module is used to determine an amount of calcium supplementation required for a regional citrate anticoagulation infusion system and the calcium pump speed control module is used to control an infusion rotation speed of the calcium pump according to the amount of calcium supplementation, and where the calcium supplementation determination module obtains the amount of calcium supplementation required in each stage of the regional citrate anticoagulation infusion system according to equations (2) and (3) or obtains the amount of calcium supplementation required in the iHD mode according to equation (12).

Based on the methods and modules for controlling the infusion rotation speed of the calcium pump and citrate pump in the above embodiments, a method for controlling the regional citrate anticoagulation infusion is also provided in another embodiment of the present disclosure, including two parts, one of which is the method for controlling the operation of the citrate pump, and the other part is the method for controlling the operation of the calcium pump. The method for controlling the regional citrate anticoagulation infusion includes the method for controlling the infusion rotation speed of the citrate pump in the embodiment corresponding to FIG. 3, and the method for controlling the infusion rotation speed of the calcium pump in the embodiment corresponding to FIG. 4.

A control system for regional citrate anticoagulation infusion is provided in another embodiment of the present disclosure. The control system includes two main modules, one of which is a module for controlling the operation of the citrate pump and the other is a module for controlling the operation of the calcium pump, i.e., a module for controlling the infusion rotation speed of the citrate pump and a module for controlling the infusion rotation speed of the calcium pump. These two main modules include the module for controlling the infusion rotation speed of the citrate pump in the embodiment corresponding to FIG. 5 and the module for controlling the infusion rotation speed of the calcium pump in the embodiment corresponding to FIG. 6.

Figure 7:
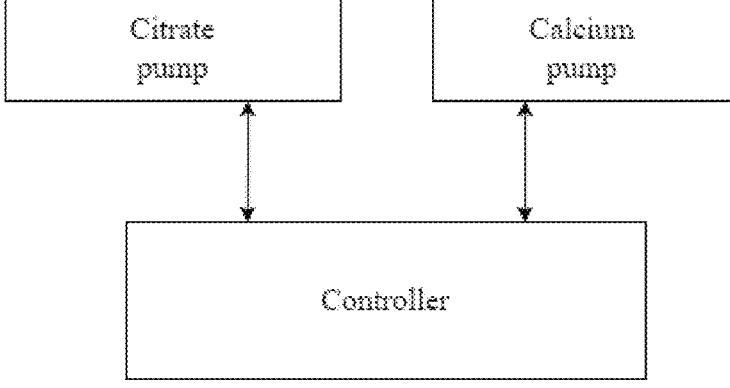
FIG. 7 is a block diagram of a regional citrate anticoagulation infusion system in one embodiment.

FIG. 7 is a block diagram of a regional citrate anticoagulation infusion system in one embodiment. The regional citrate anticoagulation infusion system includes: a citrate pump, a calcium pump, and a controller. The citrate pump is used to infuse a sodium citrate anticoagulant, the calcium pump is used to infuse a calcium chloride solution, and the controller is used to control the infusion rotation speed of the citrate pump and the calcium pump. The controller includes the module for controlling the infusion rotation speed of the citrate pump in the embodiment corresponding to FIG. 5 and the module for controlling the infusion rotation speed of the calcium pump in the embodiment corresponding to FIG. 6. This embodiment enables automatic control of regional citrate anticoagulation infusion by controlling the citrate pump and the calcium pump.

Figure 8:
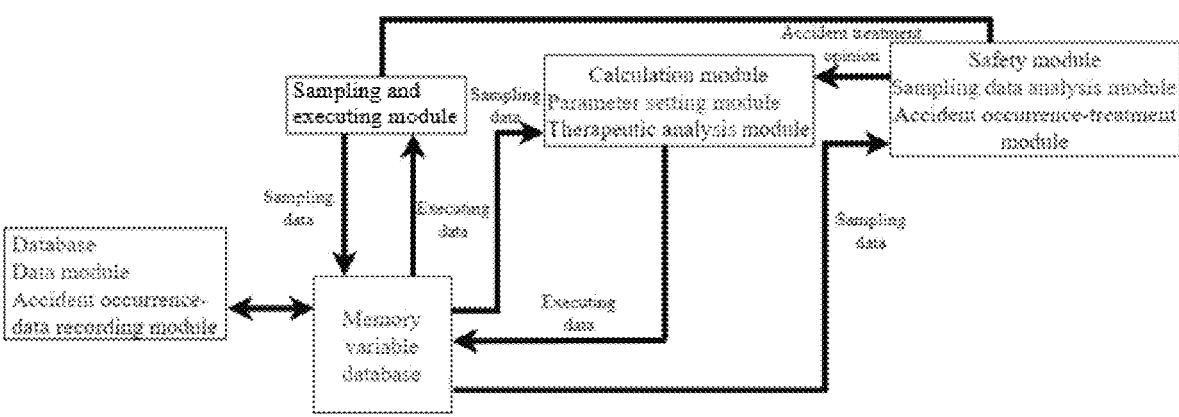
FIG. 8 is a schematic diagram of a regional citrate anticoagulation infusion system in one embodiment.

FIG. 8 is a regional citrate anticoagulation infusion system in a preferred embodiment. Based on the embodiment corresponding to FIG. 7, in the preferred embodiment of the regional citrate anticoagulation infusion system, the controller further includes: a sampling and executing module, and a therapeutic analysis module.

The sampling and executing module collects external signals and executes controller commands, which collects a plurality of parameters from the infusion tube. The sampling and executing module receives commands from the controller regarding the infusion rotation speeds of the citrate pump and the calcium pump. The sampling and executing module controls the drive motor to make the citrate pump and calcium pump work at a specified speed; for example, information such as bubble, pressure, and the status of the infusion pump's protective cover in the tube is collected by the sampling portion of the circuit, and a command regarding the infusion speed of the infusion pump from the controller is transmitted to the sampling and executing module, which controls the DC brushless motor and drive module to enable the infusion pump to operate at the specified speed.

The therapeutic analysis module regularly measures flow volumes of the citrate pump and the calcium pump. The therapeutic analysis module feeds each flow volume back to the modules for controlling the infusion rotation speeds of the citrate pump and the calcium pump, where the control modules control the infusion rotation speeds of the citrate pump and the calcium pump according to the flow volume and predetermined parameters.

In order to ensure the safety of regional citrate anticoagulation infusion, the controller further includes a safety module. The safety module analyzes the running condition of a real-time monitoring device through the sampling data, and prompts alarm and operation according to an accident that occurred in a treatment process proposed by an accident occurrence-treatment module.

In the above embodiment, the sampling and executing module, the therapeutic analysis module, and the safety module run in parallel and independently exchange data with the database.

For example, in one embodiment, the signal from the sampling module is sent to a calculation module of the MCU controller, and the calculation module exchanges data with the safety module to check whether the signal is reasonable. If the signal is reasonable, it means that the device is operating normally and the treatment will continue; if the signal is unreasonable, it means that the device is not operating normally and the accident will be classified into three levels according to the accident occurrence-treatment opinion, which include low priority, medium priority, and high priority, to take different protective measures and prompt the corresponding sound and light alarm.

In the above embodiment, the function of the therapeutic analysis module further includes:

1. receiving and analyzing in real-time the data signals transmitted from the sampling and executing module;
2. recording key data to a database or sharing the key data for recording and reading treatment records and treatment incidents by external devices;
3. analyzing patient information and therapeutic information according to a predetermined procedure, calculating in real time the desired citrate and calcium chloride infusion rotation speeds according to a two-stage theoretical model, and transmitting the signal to the sampling and executing module;
4. exchanging the sampling data in real-time with the safety module, analyzing whether the device is in a normal operation according to the accident treatment opinion and prompting protective actions and audible and visual alarms in response to the operation status of the device.

Figure 9:
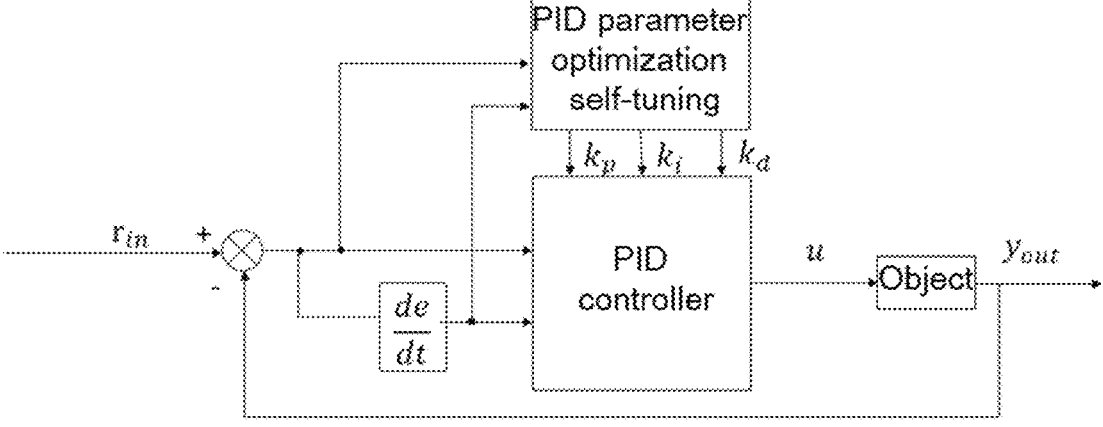
FIG. 9 is a block diagram of a single infusion pump in one embodiment.

FIG. 9 is a block diagram of a single infusion pump in one embodiment. A fuzzy adaptive tuning PID control is used for a single citrate pump or a single calcium pump. The auxiliary CRRT device or iHD device performs anticoagulation during the treatment process. During the operation of the device in the system, its characteristic parameters are highly susceptible to change because the flow rate of the CRRT device or iHD device is different from that of the device involved in the present disclosure, and the load is always changing, together with the influence of other disturbance factors such as the environment. Therefore, the fuzzy adaptive tuning PID control is applied to a single infusion pump, which identifies the characteristic parameters of the object online using the modern control theory and changes the control strategy of the single infusion pump in-real time, so that the index of the control system is always kept in the best range. During the operation of the computer, the optimal adjustment of PID parameters of a single infusion pump is automatically achieved by applying fuzzy reasoning with reference to the fuzzy control rules stored in the computer in advance and according to the actual response of the control system. Specifically, referring to FIG. 9, the equation is shown as:

$$u(k) = k_p e(k) + k_i T \sum_{j=0}^{k} e(j) + k_d \frac{e(k) - e(k-1)}{T}$$

where (j) and (k) are sampling sequence numbers, T is a sampling time constant, $k_p$ is a proportional coefficient that is inversely related to the proportion, $k_i$ is an integral coefficient, $k_d$ is a differential coefficient, e(k) is an error between a given value and a measured value, and e(k−1) is an error within the last sampling time interval. During online operation, the control system completes the online self-correction of the PID parameters by processing the results of the fuzzy logic rules, checking tables, and performing computing.

In the above-preferred embodiment, by collecting the parameters of the citrate pump and calcium chloride pump, the speeds of the citrate pump and calcium chloride pump are kept stable and manageable through PID control. And in the event of abnormalities, an alarm can be issued in time, and emergency operations can be performed at the same time, such as stopping the pump's infusion.

Figure 10:
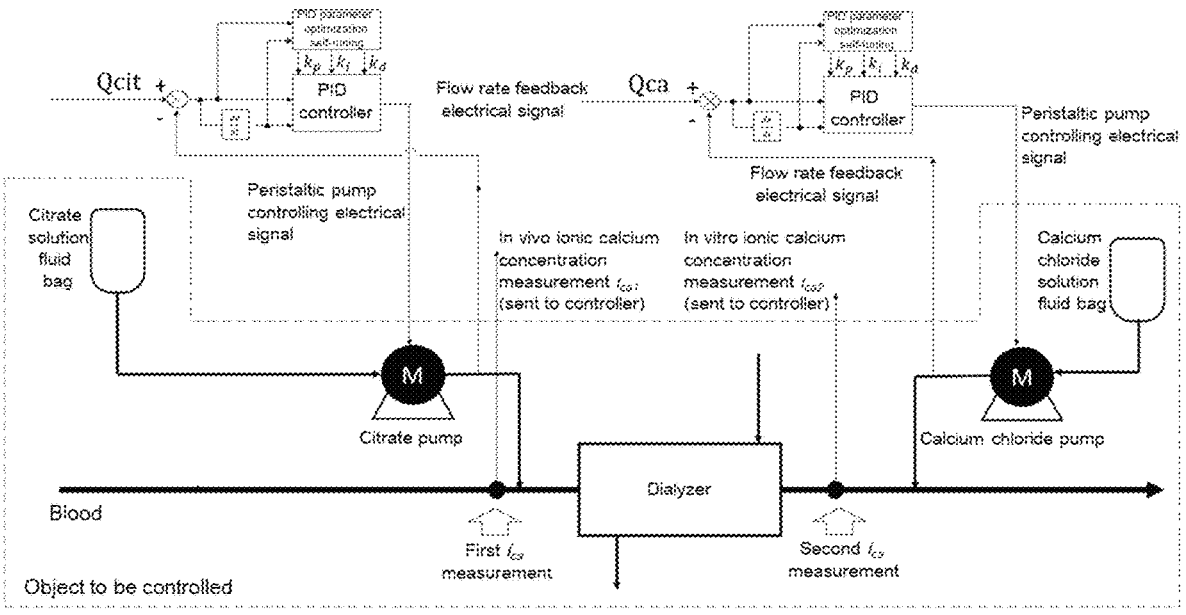
FIG. 10 is a schematic control principle diagram of a regional citrate anticoagulation infusion system in one embodiment.

FIG. 10 is a schematic control principle diagram of a regional citrate anticoagulation infusion system in one embodiment. In practice, the patient's blood is drawn from the body, afterward, it passes through a dialyzer and then is returned to the body, where an injection of sodium citrate anticoagulant to the blood channel via a citrate infusion pump is required before the blood enters the dialyzer, at the same time, an injection of calcium chloride solution to the blood channel via a calcium chloride infusion pump is required before the blood returns to the body to supplement the patient's lost calcium. The overall control in this embodiment includes two aspects, in the first aspect, two peristaltic pumps (i.e., the citrate pump and the calcium chloride pump) are respectively in a closed-loop control, and in the second aspect, a controller is provided for intelligent analysis and decision-making, and the controller can be implemented by using software modules or hardware devices. As shown in FIG. 10, the main input parameter of the citrate pump is Qcit, the output parameter is the rotation speed signal of the citrate pump, and the rotation speed of the citrate pump is kept stable and manageable by PID control. The main input parameter of the calcium chloride pump is Qca, the output parameter is the rotation speed signal of the calcium chloride pump, and the rotation speed of the calcium chloride pump is kept stable and manageable by PID control. Meanwhile, during the treatment process, it is required to measure the levels of calcium ions in the blood before and after the blood passes through the dialyzer, respectively, and then input the levels of calcium ions into the system. The controller will automatically adjust the infusion speed of the calcium chloride pump.

The controller collects the basic parameters of the patient and the parameters of the extracorporeal blood purification treatment, and then the therapeutic analysis module calculates the flow rates of citrate and calcium per hour according to the "two-stage calcium supplement theory", citrate pharmacokinetics theory, and blood purification kinetics theory. These flow rates are automatically converted into the operating parameters of drive motors through the closed-loop control of the citrate pump and the calcium chloride pump, respectively. The drive motors of the citrate pump and the calcium chloride pump drive their respective pump heads of peristaltic pumps through deceleration mechanisms. The rotor on the pump head repeatedly squeezes the outer wall of the infusion tube to enable the continuous directional flow of the drug solution in the tube, thus achieving the purpose of precise fluid infusion.

Figure 11:
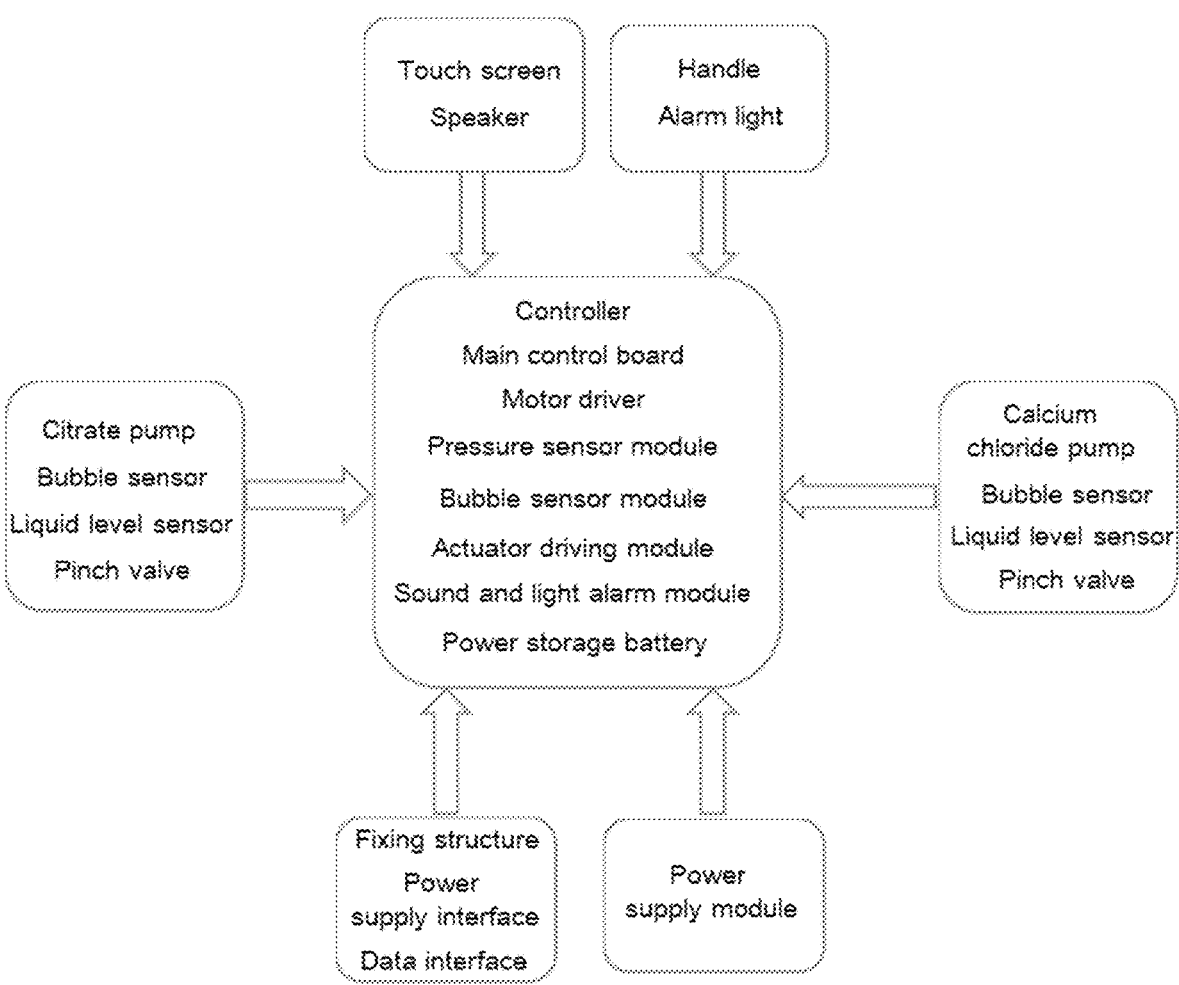
FIG. 11 is a structural block diagram of a regional citrate anticoagulation infusion system in one embodiment.

FIG. 11 shows a structural block diagram of a regional citrate anticoagulation infusion system in one embodiment. A citrate pump, a bubble sensor, a liquid level sensor, and a pinch valve constitute a citrate infusion system. A calcium chloride pump, a bubble sensor, a liquid level sensor, and a pinch valve constitute a calcium chloride infusion system. A controller includes a main control board, a motor driver, a pressure sensor module, a bubble sensor module, an actuator driving module, and a sound and light alarm module and its power storage battery. The system may also be provided with a shell, which is equipped with a shell fixing structure, an air outlet, an external power supply interface and a data interface, a touch screen, a speaker, an alarm light, and other components. The regional citrate anticoagulation infusion system achieves the collection of the above-mentioned parameters in each part, the control of the citrate pump, the control of the calcium chloride pump (calcium pump), the detection, alarm, and emergency stop in abnormal situations, as well as other functions. The sodium citrate solution and calcium chloride solution flow in two non-interfering channels in the treatment process. In an embodiment, the liquid channel of the sodium citrate solution is used to describe the workflow of the system as an example, which is the same as that of the calcium chloride solution. Specifically, the sodium citrate solution is pumped out from the fluid bag to the infusion pump. Before entering the infusion pump, the sodium citrate solution passes through a first bubble sensor. If the fluid bag is empty, the bubble sensor detects bubbles in the liquid channel, and then the system alarms and prompts to change the fluid bag. After passing through the infusion pump, the sodium citrate solution enters a first intravenous pot, which is placed in a liquid level sensor. The upper branch of the intravenous pot is connected to the joint of a pressure sensor through the protective cover of the pressure sensor, the other end of the intravenous pot is connected to a pressure detection module on a main board and to a small air pump. If the fluid level in the intravenous pot is lower than the fluid level set by the system, the small air pump will adjust the fluid level in the intravenous pot to a normal level, meanwhile, the pressure detection module will monitor the pressure change in real-time and adjust the flow rate of the infusion pump through the pressure compensation of the system, so that the infusion pump can ensure the accuracy of the flow rate no matter what pressure load it works under. The sodium citrate solution enters a second bubble sensor after passing through the intravenous pot to detect whether there are bubbles in the sodium citrate solution flowing to the blood extracorporeal circulation circuit and then enters a pinch valve after passing through the second bubble sensor. If bubbles are detected, the system shuts down the infusion pump and the pinch valve to ensure that the bubbles do not enter the blood extracorporeal circulation circuit. The bubbles can be eliminated by opening the pinch valve, the small air pump will pump out the bubbles, and then the machine will resume operation.

In another embodiment of the present disclosure, an electronic device is provided. The electronic device includes a memory, a processor, and a computer program stored in the memory and executed on the processor. When the processor executes the computer program, one of the following methods is performed: the method for controlling the infusion rotation speed of the citrate pump; the method for controlling the infusion rotation speed of the calcium pump; and the method for controlling the regional citrate anticoagulation infusion.

In another embodiment of the present disclosure, a computer-readable storage medium is provided, having a computer program stored thereon, when the processor executes the computer program, one of the following methods is performed: the method for controlling the infusion rotation speed of the citrate pump; the method for controlling the infusion rotation speed of the calcium pump; and the method for controlling the regional citrate anticoagulation infusion.

The memory described above may include volatile memory, such as random access memory (RAM), static random-access memory (SRAM), double data rate synchronous dynamic random access memory (DDR SDRAM), etc., and may also include non-volatile memory, such as flash memory. The memory is used to store computer programs (such as applications, functional modules, etc. that implement the above method), computer instructions, etc., and the above computer programs, computer instructions, and the like may be stored in one or more memories. And the above computer programs, computer instructions, data, and the like can be called by the processor.

The processor is used to execute the computer program stored in the memory to implement the various steps in the method involved in the above embodiments. The relevant descriptions of the methods can be seen in the previous embodiments.

The processor and the memory may be separate structures or integrated into a single structure. When the processor and the memory are independent structures, the memory and the processor may be in a coupling connection via a bus.

It should be noted that the steps of the method provided by the present disclosure can be implemented by using the corresponding modules, devices, units, etc. in the system, and a person skilled in the art can implement the step flow of the method with reference to the technical solution of the system, i.e., the embodiments of the system are preferred examples for implementing the method, which will not be repeated herein.

It is known to those skilled in the art that, except for an absolute computer readable program code manner, the system and its devices provided by the present disclosure may be realized in the forms of logic gates, switches, special integrated circuits, programmable logic controllers, and embedded microcontrollers, and the like by programming the steps of the method logically. Therefore, the system and its various devices provided by the present disclosure may be considered as a hardware component, and the devices included therein for implementing various functions may also be considered as structures within the hardware component. Alternatively, the devices for implementing various functions may be considered as software modules for implementing the method or structures within the hardware component.

Specific embodiments of the present disclosure have been described above. It should be understood that the above embodiments of the present disclosure are not intended to limit the implementations of the present disclosure. For those of ordinary skill in the art, changes or variations can be made within the protection scope of the present disclosure, which does not affect the substance of the present disclosure. Each of the above features may be used in combination without conflict with each other.

The invention claimed is:

1. A module for controlling an infusion rotation speed of a calcium pump, comprising:
   a calcium pump speed control module, for controlling the infusion rotation speed of the calcium pump according to an amount of calcium supplementation required for a regional citrate anticoagulation infusion system, which is referred to as Qca; and
   a calcium supplementation determination module coupled to the calcium pump speed control module,
   wherein upon being in a post-dilution CVVHD mode, the calcium supplementation determination module is configured to:
   calculate an amount of calcium supplementation required in each stage of a two-stage calcium supplement model,
   obtain an amount of calcium supplementation required in a first stage, which is referred to as Qca1, wherein $$Qca1(\text{mmol}/h) = \frac{fa \times \text{Cca\_T} \times Cln - ca \times 60)}{1000} + fb \times Csys(t) \times BW(kg) \times 25\%, \text{ and}$$

obtain an amount of calcium supplementation required in a second stage, which is referred to as Qca2; , wherein $$Qca2(\text{mmol}/h) = \frac{fa \times \text{Cca\_T} \times Cln - ca \times 60}{1000},$$

wherein fa is a fraction of dispersable calcium at an upstream of a dialyzer after a citrate infusion at an arterial end, Cca_T is a total calcium concentration at the upstream of the dialyzer after the citrate infusion, Cln-ca is a dispersable calcium clearance, fb is a correlation coefficient between an accumulated calcium concentration and a citrate concentration, Csys (t) is the citrate concentration at different time, and BW is a weight of a patient;
   wherein upon being in an intermittent hemodialysis (iHD) mode, the calcium supplementation determination module is configured to:
   calculate the dispersable calcium clearance Cln-ca after selecting a membrane area for the dialyzer,
      wherein when the membrane area is less than 1.2 m$^2$, Cln-Ca=0.7944×(Qb×0.43+80.5)×(1−Hct)+2.2421+ 0.46×Quf;
      wherein when the membrane area ranges from 1.2 to 1.8 m$^2$, Cln-Ca=0.7944×(Qb×0.29+95)×(1−Hct)+2.2421+ 0.46×Quf;

wherein when the membrane area is greater than 1.8 m$^2$, Cln-Ca=0.7944×(Qb×0.53+75.5)×(1−Hct)+2.2421+ 0.46×Quf;

calculating the amount of calcium cleared in extracorporeal circulation per hour, which is referred to as Eca (mmol/L), based on the dispersable calcium clearance Cln-ca, wherein Eca (mmol/L)=fa×Cca_T×Cln-ca×60/1000 wherein the amount of calcium cleared in extracorporeal circulation is the amount of calcium supplementation, Qb is a blood flow velocity, Quf is an ultrafiltration rate, and Hct is a red blood cell hematocrit;

wherein a fuzzy adaptive tuning PID control is used for the calcium pump, and, according to a response of the system, a fuzzy inference is applied with reference to fuzzy control rules stored in advance in a computer to automatically achieve an optimal adjustment of PID parameters of the calcium pump; and wherein the calcium pump speed control module is included in a controller of the regional citrate anticoagulation infusion system, the Qca is a main input parameter to the controller for controlling the calcium pump, and upon applying the fuzzy adaptive tuning PID control, the controller outputs a peristaltic pump controlling electrical signal to the calcium pump, the infusion rotation speed of the calcium pump being automatically adjusted in response to a change in the Qca to keep the infusion rotation speed of the calcium pump stable.

2. A control system for a regional citrate anticoagulation infusion, comprising:

the module for controlling the infusion rotation speed of the calcium pump according to claim 1; and a module for controlling an infusion rotation speed of a citrate pump, comprising:

a citrate pump speed control module, for controlling the infusion rotation speed of the citrate pump according to a citrate infusion volume per unit time, which is referred to as Qcit, wherein Qcit (mmol/h)=4−5 (mmol/L)×Qb (ml/min)×(1−Hct%)

wherein Qb is the blood flow velocity, and Hct is the red blood cell hematocrit;

wherein the fuzzy adaptive tuning PID control is further used for the citrate pump; and, according to the response of the system, the fuzzy inference is further applied with reference to the fuzzy control rules stored in advance in the computer to automatically achieve an optimal adjustment of PID parameters of the citrate pump;

wherein the citrate pump speed control module is included in the controller of the regional citrate anticoagulation infusion system, the Qcit is a main input parameter to the controller for controlling the citrate pump, and upon applying the fuzzy adaptive tuning PID control, the controller outputs a peristaltic pump controlling electrical signal to the citrate pump, the infusion rotation speed of the citrate pump being automatically adjusted in response to a change in the Qcit to keep the infusion rotation speed of the citrate pump stable.

3. A regional citrate anticoagulation infusion system, comprising:

a controller, comprising:

the module for controlling the infusion rotation speed of the calcium pump according to claim 1; and a module for controlling an infusion rotation speed of a citrate pump, comprising:

a citrate pump speed control module, for controlling the infusion rotation speed of the citrate pump according to a citrate infusion volume per unit time, which is referred to as Qcit, wherein Qcit (mmol/h)=4−5 (mmol/L)×Qb (ml/min)×(1−Hct%)

wherein Qb is the blood flow velocity, and Hct is the red blood cell hematocrit;

the citrate pump connected to the module for controlling an infusion rotation speed of a citrate pump, for infusing a sodium citrate solution; and the calcium pump connected to the module for controlling the infusion rotation speed of the calcium pump, for infusing a calcium chloride solution;

wherein the fuzzy adaptive tuning PID control is further used for the citrate pump; and, according to the response of the system, the fuzzy inference is further applied with reference to the fuzzy control rules stored in advance in the computer to automatically achieve an optimal adjustment of PID parameters of the citrate pump;

wherein the citrate pump speed control module is included in the controller of the regional citrate anticoagulation infusion system, the Qcit is a main input parameter to the controller for controlling the citrate pump, and upon applying the fuzzy adaptive tuning PID control, the controller outputs a peristaltic pump controlling electrical signal to the citrate pump, the infusion rotation speed of the citrate pump being automatically adjusted in response to a change in the Qcit to keep the infusion rotation speed of the citrate pump stable.

4. The regional citrate anticoagulation infusion system according to claim 3, wherein the controller further comprises a therapeutic analysis module configured to:

record sampling data to a database or share the sampling data for recording and reading treatment records and treatment incidents by external devices;

analyze patient information and therapeutic information according to a predetermined procedure, and calculate in real time desired citrate and calcium chloride infusion speeds according to a two-stage theoretical model;

analyze whether a device is in normal operation according to an accident treatment opinion and prompt protective actions and audible and visual alarms in response to an operation status of the device.

5. An electronic device, comprising a memory, a processor, and a computer program stored in the memory and executed on the processor, wherein the processor operates the module for controlling the infusion rotation speed of the calcium pump according to claim 1 or a control system for a regional citrate anticoagulation infusion by executing the computer program;

wherein the control system for the regional citrate anticoagulation infusion comprises:

the module for controlling the infusion rotation speed of the calcium pump according to claim 1; and a module for controlling an infusion rotation speed of a citrate pump, comprising:

a citrate pump speed control module, for controlling the infusion rotation speed of the citrate pump according to a citrate infusion volume per unit time, which is referred to as Qcit, wherein Qcit (mmol/h)=4−5 (mmol/L)×Qb (ml/min)×(1−Hct%)

wherein Qb is the blood flow velocity, and Hct is the red blood cell hematocrit;

wherein the fuzzy adaptive tuning PID control is further used for the citrate pump; and, according to the response of the system, the fuzzy inference is further applied with reference to the fuzzy control rules stored in advance in the computer to automatically achieve an optimal adjustment of PID parameters of the citrate pump;

wherein the citrate pump speed control module is included in the controller of the regional citrate anticoagulation infusion system, the Qcit is a main input parameter to the controller for controlling the citrate pump, and upon applying the fuzzy adaptive tuning PID control, the controller outputs a peristaltic pump controlling electrical signal to the citrate pump, the infusion rotation speed of the citrate pump being automatically adjusted in response to a change in the Qcit to keep the infusion rotation speed of the citrate pump stable.

6. A computer-readable storage medium, having a computer program stored thereon, wherein the module for controlling the infusion rotation speed of the calcium pump according to claim 1 or a control system for a regional citrate anticoagulation infusion is operated when the computer program is executed by a processor, wherein the control system for the regional citrate anticoagulation infusion comprises:

the module for controlling the infusion rotation speed of the calcium pump according to claim 1; and a module for controlling an infusion rotation speed of a citrate pump, comprising:

a citrate pump speed control module, for controlling the infusion rotation speed of the citrate pump according to a citrate infusion volume per unit time, which is referred to as Qcit, wherein $$Qcit \text{ (mmol/h)} = 4 \text{--} 5 \text{ (mmol/L)} \times Qb \text{ (ml/min)} \times (1 \text{--} Hct\%)$$

wherein Qb is the blood flow velocity, and Hct is the red blood cell hematocrit;

wherein the fuzzy adaptive tuning PID control is further used for the citrate pump; and, according to the response of the system, the fuzzy inference is further applied with reference to the fuzzy control rules stored in advance in the computer to automatically achieve an optimal adjustment of PID parameters of the citrate pump;

wherein the citrate pump speed control module is included in the controller of the regional citrate anticoagulation infusion system, the Qcit is a main input parameter to the controller for controlling the citrate pump, and upon applying the fuzzy adaptive tuning PID control, the controller outputs a peristaltic pump controlling electrical signal to the citrate pump, the infusion rotation speed of the citrate pump being automatically adjusted in response to a change in the Qcit to keep the infusion rotation speed of the citrate pump stable.

7. The regional citrate anticoagulation infusion system according to claim 3, further comprising a citrate infusion system including:

a fluid bag containing a sodium citrate solution;

a first bubble sensor arranged on a liquid channel between the fluid bag and the citrate pump and configured to detect whether bubbles are present in the sodium citrate solution flowing from the fluid bag toward the citrate pump;

a first intravenous pot connected to the citrate pump and placed in a liquid level sensor configured to detect a liquid level in the first intravenous pot;

a pressure sensor having a protective cover and connected to an upper branch of the first intravenous pot through the protective cover;

a pressure detection module disposed on a main control board of the controller connected to another branch of the first intravenous pot;

a second bubble sensor arranged downstream of the first intravenous pot on the liquid channel and configured to detect whether bubbles are present in the sodium citrate solution flowing from the first intravenous pot toward a blood extracorporeal circulation circuit; and a pinch valve arranged on the liquid channel between the second bubble sensor and the blood extracorporeal circulation circuit.

8. The regional citrate anticoagulation infusion system according to claim 7, wherein upon the fluid bag being empty, the first bubble sensor detects bubbles in the sodium citrate solution in the liquid channel and the controller is configured to generate an alarm and to prompt replacement of the fluid bag.

9. The regional citrate anticoagulation infusion system according to claim 7, wherein upon the liquid level sensor detecting that the liquid level in the first intravenous pot is lower than a fluid level set by the system, and the pressure detection module is configured to monitor a pressure change in real time and to adjust a flow rate of the citrate pump through pressure compensation so that the citrate pump ensures accuracy of the flow rate under different pressure loads.

10. The regional citrate anticoagulation infusion system according to claim 7, wherein upon the second bubble sensor detecting bubbles in the sodium citrate solution flowing toward the blood extracorporeal circulation circuit, the controller is configured to shut down the citrate pump and to close the pinch valve to prevent the bubbles from entering the blood extracorporeal circulation circuit.

* * * * *